(12) United States Patent
West

(10) Patent No.: US 6,692,510 B2
(45) Date of Patent: Feb. 17, 2004

(54) ANEURYSM EMBOLIZATION DEVICE AND DEPLOYMENT SYSTEM

(75) Inventor: Clinton B. West, Pembroke Pines, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

(21) Appl. No.: 10/141,411

(22) Filed: May 8, 2002

(65) Prior Publication Data

US 2003/0212419 A1 Nov. 13, 2003

Related U.S. Application Data

(60) Provisional application No. 60/298,324, filed on Jun. 14, 2001.

(51) Int. Cl.[7] ............................................. A61M 29/00
(52) U.S. Cl. ....................................... 606/191; 606/195
(58) Field of Search ................................. 606/191, 195

(56) References Cited

U.S. PATENT DOCUMENTS

| 3,095,877 | A |   | 7/1963  | Rowan |
| 5,263,964 | A |   | 11/1993 | Purdy |
| 5,443,478 | A |   | 8/1995  | Purdy |
| 5,527,338 | A |   | 6/1996  | Purdy |
| 5,693,067 | A |   | 12/1997 | Purdy |
| 5,749,894 | A | * | 5/1998  | Engelson ..................... 606/213 |
| 5,833,642 | A |   | 11/1998 | McCabe et al. |
| 5,843,118 | A |   | 12/1998 | Sepetka et al. |
| 5,925,059 | A | * | 7/1999  | Palermo et al. ............. 606/191 |
| 5,941,888 | A |   | 8/1999  | Wallace et al. |
| 6,004,338 | A | * | 12/1999 | Ken et al. .................... 606/191 |
| 6,063,100 | A | * | 5/2000  | Diaz et al. ................... 606/191 |
| 6,068,644 | A | * | 5/2000  | Lulo et al. ................... 606/191 |
| 6,136,015 | A |   | 10/2000 | Kurz et al. |
| 6,159,206 | A |   | 12/2000 | Ogawa |
| 6,183,491 | B1 |  | 2/2001  | Lulo |
| 6,203,556 | B1 |  | 3/2001  | Evans et al. |
| 6,238,403 | B1 |  | 5/2001  | Greene, Jr. et al. |
| 6,299,619 | B1 |  | 10/2001 | Greene, Jr. et al. |

FOREIGN PATENT DOCUMENTS

| EP | 0 948 935 A1 | 10/1999 |
| WO | WO 00/72781 A2 | 12/2000 |

* cited by examiner

*Primary Examiner*—Gary Jackson
(74) *Attorney, Agent, or Firm*—Henry W. Collins

(57) ABSTRACT

An aneurysm embolization device and deployment system for use in occluding the flow of blood at a preselected position within a vessel of the human body comprising a headpiece and a plurality of spherical members linked together with a central connecting member, which, when deployed the embolization device occludes the flow of blood in a high volume or wide neck aneurysm.

18 Claims, 3 Drawing Sheets

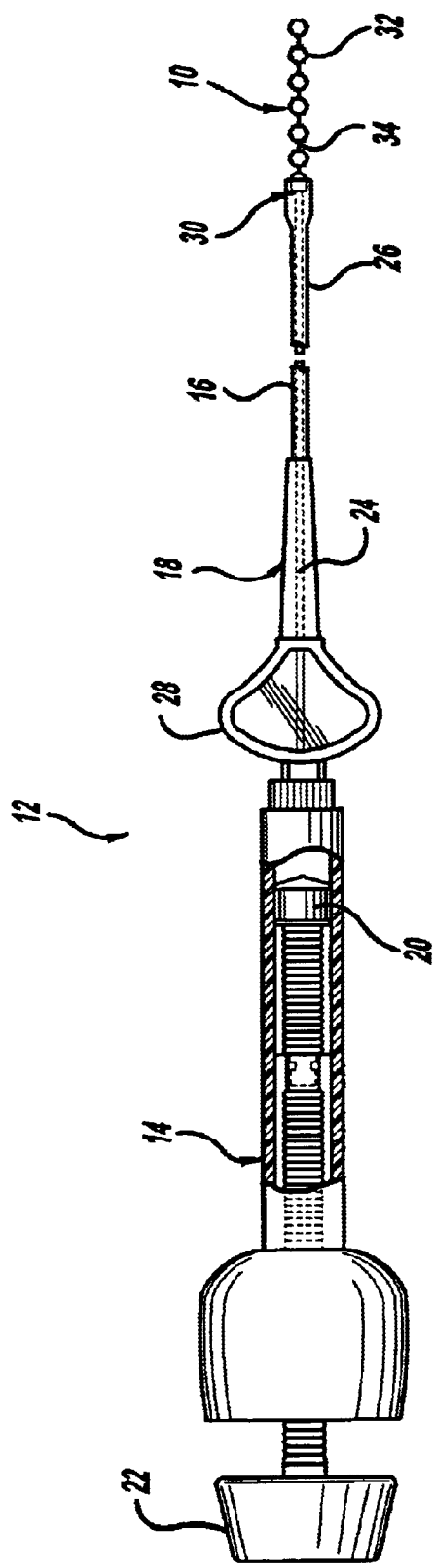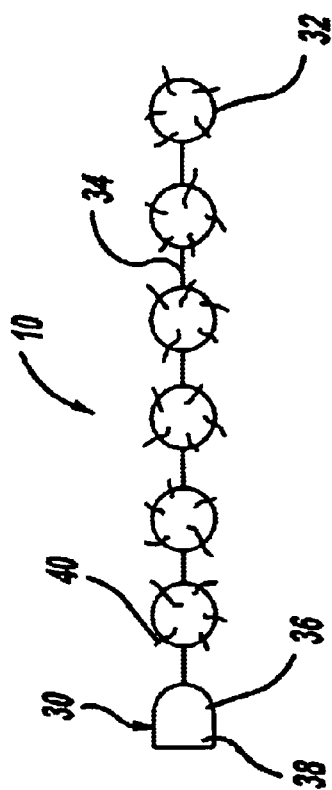
*Figure - 1*
*Figure - 2*

US 6,692,510 B2

ANEURYSM EMBOLIZATION DEVICE AND DEPLOYMENT SYSTEM

This patent application claims the benefit of provisional patent application Ser. No. 60/298,324 filed on Jun. 14, 2001.

BACKGROUND OF THE INVENTION

1. Field of the Invention

This invention relates to a medical apparatus and method for occluding the flow of blood at a preselected position within a vessel of the human body, and more particularly, relates to an aneurysm embolization device for filling a high volume or wide neck aneurysm and a deployment system for releasing the embolization device within the aneurysm.

2. Description of the Prior Art

For many years physicians have been placing various devices within a blood vessel of the human body in order to treat an aneurysm by promoting thrombus formation. Such devices include balloons, coils, fiber retainers, multi-element anchors, and micropellets. Balloons are introduced into an aneurysm using a deployment catheter and then inflated within the aneurysm. The balloon prevents the flow of blood within the parent vessel from entering the aneurysm.

Another type of occluding device is an embolic coil. Embolic coils may take the form of helically wound coils, randomly wound coils, coils wound within other coils, or many other coil configurations. These coils are generally formed of metallic materials, such as platinum, gold, and tungsten, or alloys of these metals. Often times, several coils need to be placed within an aneurysm in order to occlude the flow of blood.

Furthermore, a retainer which holds at least one fiber bundle can occlude the flow of blood. The retainer can take the form of a cube, sphere, cylinder, coil, oval, or other similar shape. The thrombogenic fibers are longer than the retainer and can be made of silk, cotton, nylon, or polyurethane. These fiber bundles occlude the flow of blood in a vessel. This device is primarily used in small vessels of the vasculature.

Also, a multi-element occlusion device can stop the flow of blood in a vessel. This device has two or more elements connected by at least one metallic or nonmetallic fiber. The elements can be particles or coils with various sizes and shapes. The device is deployed with a catheter and flows downstream until the anchoring element lodges against the vessel wall. The multiple elements connected to the anchor help create deep occlusion. This device cuts off the flow of blood in a vessel and reduces the risk of continued canalization within the vessel.

Finally, micropellets are cylindrical members formed from a biocompatible foam or gel material. Several micropellets can be linked together with a carrier wire and when the micropellets are soaked in a fluid, they expand to fill an aneurysm. The swelled micropellets occlude the flow of blood and become fixed within the aneurysm.

Balloons, coils, fiber retainers, multi-element anchors, and micropellets are devices beneficial in treating aneurysms. However, the present invention is useful in treating large aneurysms or wide neck aneurysms. The present invention is an embolization device which occludes the flow of blood in an aneurysm, reduces the risk of becoming dislodged, allows blood to continue flowing through the parent vessel, and allows for retrieval or realignment.

SUMMARY OF THE INVENTION

In accordance with one aspect of the present invention, an aneurysm embolization device and deployment system is provided for use in placing the aneurysm embolization device at a preselected position within a vessel of the body. The deployment system includes a deployment catheter formed of a material which is sufficiently flexible to pass through the vasculature of the body. The proximal section of the catheter has substantially no radial expansion when fluid pressure is applied to the lumen of the catheter. The distal section of the catheter expands radially when fluid pressure is applied. The deployment system also includes a headpiece. The distal section of the headpiece is hemispherical in shape while the proximal section of the headpiece is cylindrical and is disposed within the lumen of the deployment catheter. Furthermore, the deployment system includes a central connecting member. The central connecting member is a flexible fiber which is attached at one end to the headpiece. The deployment system also includes a spherical member. The spherical member is a small diameter ball and is disposed about the central connecting member. Finally, the proximal section of the deployment catheter includes a connector. The connecter is adapted for a fluid pressure generating device and is used for applying fluid pressure to the lumen of the deployment catheter causing the distal section of the catheter to expand radially thereby releasing the headpiece and deploying the aneurysm embolization device.

In accordance with another aspect of the present invention, an aneurysm embolization device is provided for use in occluding the flow of blood at a preselected position within a vessel of the human body. The aneurysm embolization device includes a headpiece. The distal section of the headpiece is hemispherical in shape while the proximal section of the headpiece is cylindrical and is disposed within a deployment catheter. The aneurysm embolization device also includes a central connecting member. The central connecting member is a flexible fiber which is attached at one end to the headpiece. Finally, the aneurysm embolization device includes a spherical member. The spherical member is a small diameter ball and is disposed about the central connecting member.

In accordance with a similar aspect of the present invention, the headpiece and spherical member are made of a polymer or metallic material.

In accordance with a similar aspect of the present invention, the headpiece and spherical member are made of a metallic material.

In accordance with a similar aspect of the present invention, the central connecting member takes the form of a shape memory wire. After the aneurysm embolization device is deployed within the vasculature of the body, the wire tends to assume a predetermined configuration.

In accordance with another similar aspect of the present invention, the central connecting member takes the form of a stretchable fiber.

In accordance with a similar aspect of the present invention, the headpiece includes a pocket which takes the form of a concave indentation on the headpiece at a position where the central connecting member attaches to the headpiece. As a result, the central connecting member can coil up into the pocket during deployment.

In accordance with another similar aspect of the present invention, the spherical member includes a pocket which takes the form of a concave indentation on the spherical member at a position where the central connecting member attaches to the spherical member. As a result, the central connecting member can coil up into the pocket during deployment.

In accordance with a similar aspect of the present invention, the spherical member includes a plurality of filaments which are attached generally radial to the spherical member. The filaments enhance the occlusive effect of the spherical member.

In accordance with another aspect of the present invention, the spherical member includes a time-released adhesive on the periphery of the spherical member. The adhesive enhances the occlusive effect of the spherical member.

In accordance with another aspect of the present invention, the aneurysm embolization device and deployment system includes six spherical members.

In accordance with another aspect of the present invention, a method is provided for placing an aneurysm embolization device at a pre-selected position within a vessel. The method includes providing a delivery catheter having an elongated flexible tube and introducing the deliver catheter into the vasculature of the human body. The method also includes providing a deployment system having a deployment catheter. The proximal section of the catheter exhibits the characteristic of having substantially no radial expansion when fluid pressure is applied to the lumen of the catheter. The distal section of the catheter exhibits the characteristic that, when fluid pressure is applied to the lumen of the catheter the distal section of the catheter expands radially. The method further includes providing an aneurysm embolization device having a headpiece disposed within the deployment catheter. The aneurysm embolization device also includes a central connecting member which takes the form of a flexible fiber. The proximal end of the connecting member is attached to the headpiece. Finally, the embolization device includes a spherical member which takes the form of a small diameter ball. The spherical member is disposed about the central connecting member. The method further includes introducing the deployment system and the aneurysm embolization device into the delivery catheter and aligning the aneurysm embolization device with the pre-selected position within the vessel. The method finally includes applying fluid pressure to the deployment catheter causing the distal section of the deployment catheter to expand radially thereby releasing the aneurysm embolization device.

These aspects of the invention and the advantages thereof will be more clearly understood from the following description and drawings of the preferred embodiment.

BRIEF DESCRIPTION OF THE DRAWINGS

FIG. 1 is an enlarged, partially sectioned view of an aneurysm embolization device and deployment system where the aneurysm embolization device is disposed within a deployment catheter of the deployment system;

FIG. 2 is an enlarged perspective view showing an aneurysm embolization device with a headpiece, six spherical members linked to the headpiece with a central connecting member, and filaments attached to the spherical members;

DESCRIPTION OF THE PREFERRED EMBODIMENT

Figure 3:
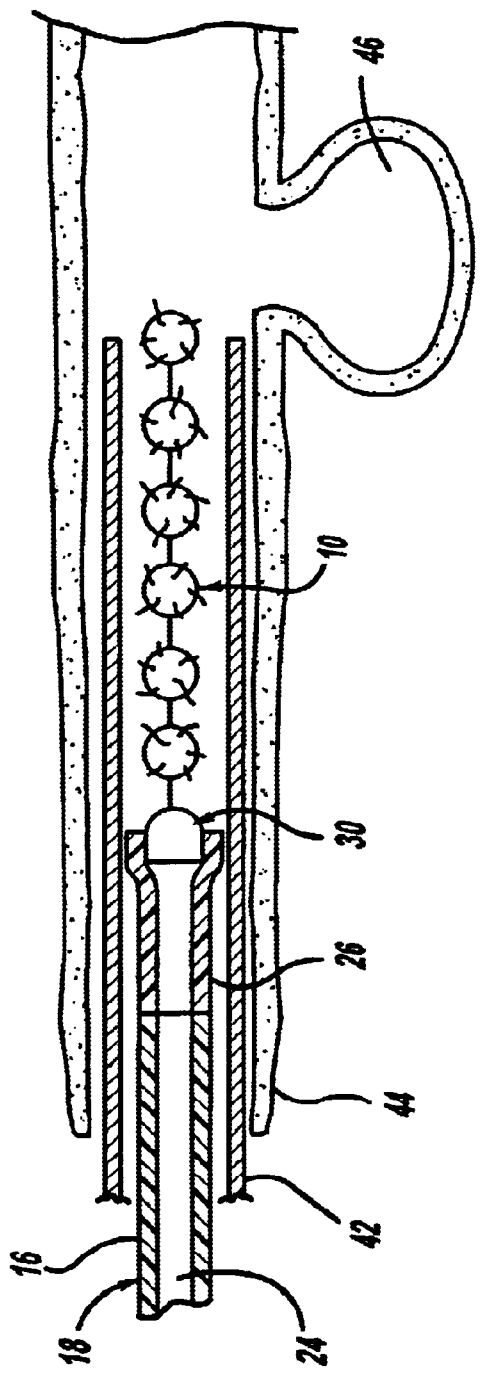
FIG. 3 is an enlarged, partially sectioned view of the aneurysm embolization device disposed within the deployment catheter and being transported through a delivery catheter.

FIG. 1 illustrates an aneurysm embolization device 10 and deployment system 12 which includes a syringe 14 coupled to the proximal section 16 of a deployment catheter 18. The syringe 14 includes a threaded piston 20 which is controlled by a handle 22 for infusing fluid into a lumen 24 of the deployment catheter 18. The aneurysm embolization device 10 is disposed within the lumen 24 of the distal section 26 of the deployment catheter 18. Also, the deployment catheter 18 includes a winged hub 28 which aides in the insertion of the deployment catheter 18 into the vasculature of the human body.

FIG. 2 illustrates an aneurysm embolization device 10 which includes a headpiece 30, six spherical members 32, and a central connecting member 34 linking the headpiece 30 and spherical members 32 together. Preferably, the length of the aneurysm embolization device 10 may range from about 0.102 inches to about 0.32 inches with a preferred length of approximately 0.148 inches. The spherical members 32 are made of a polymer material, but may be made of other biocompatible materials like stainless steel or platinum. Whether made of a polymer or metallic material, the spherical members 32 are not expandable (non-expanding) so that the aneurysm embolization device 10 can be retrieved or realigned. Preferably, the diameter of a spherical member 32 may range from about 0.012 inches to about 0.020 inches. In the preferred embodiment, the diameter of a spherical member 32 is approximately 0.016 inches. The spherical members 32 may be molded around or bonded to the central connecting member 34. The ball-like shape of the spherical members 32 allows the aneurysm embolization device 10 to flex and assume complex configurations thereby substantially filling a high volume aneurysm. The central connecting member 34 may be made of Nitinol which is a shape memory material. The connecting member 34 may also be made of other materials like stainless steel, platinum, or a polymer. Preferably, the length of the central connecting member 34 between the spherical members 32 may range from about 0.0015 inches to about 0.015 inches. In the preferred embodiment, the length of the central connecting member 34 between the spherical members 32 is approximately 0.006 inches. The headpiece 30 is made of a polymer material, but may be made of other biocompatible materials like stainless steel or platinum. Preferably, the length of the headpiece 30 may range from about 0.012 inches to about 0.020 inches. In the preferred embodiment, the length of the headpiece 30 is approximately 0.016 inches. The distal section 36 of the headpiece 30 is hemispherical in shape and has a radius generally equal to one half the length of the headpiece 30. In the preferred embodiment, the radius of the distal section 36 of the headpiece 30 is approximately 0.008 inches. The proximal section 38 of the headpiece 30 is cylindrical in shape and has a radius generally equal to the radius of the distal section 36 of the headpiece 30. Filaments 40 are molded into or bonded with the spherical members 32. The filaments 40 are made of nylon but may also be made of acrylic or a polymer.

Preferably, the length of the filaments 40 may range from about 0.003 inches to about 0.010 inches. In the preferred embodiment, the length of the filaments 40 is approximately 0.005 inches. The filaments 40 may cover the surface of a spherical member 32 from 0 percent to 50 percent; there is a coverage area of about 10 percent in the preferred embodiment.

FIG. 3 illustrates the deployment catheter 18 with the aneurysm embolization device 10 during transportation through a delivery catheter 42 positioned in a vessel 44. The headpiece 30 is tightly held within the lumen 24 of the deployment catheter 18. In this position, the headpiece 30 serves to provide a fluid-tight seal at the distal section 26 of the deployment catheter 18.

Preferably, the proximal section 16 of the deployment catheter 18 is formed of Pebax material having a durometer in a range of about 62D to 75D. The proximal section 16 is sufficiently flexible to transverse the vasculature of the human body, but is sufficiently rigid such that, when fluid pressure of approximately 90 to 450 psi is applied to the lumen 24 of the deployment catheter 18 there is very little, if any, radial expansion of the proximal section 16. The distal section 26 of the deployment catheter 18 is preferably formed of polymer material with a relatively low durometer which exhibits the characteristic that, when fluid pressure of approximately 90 to 450 psi is applied to the lumen 24 of the deployment catheter 18 the distal section 26 expands radially thereby releasing the aneurysm embolization device 10. The distal section 26 of the deployment catheter 18 is preferably formed of Pebax material having a durometer of between 25D and 55D with a durometer of 40D being the preferred durometer.

Figure 4:
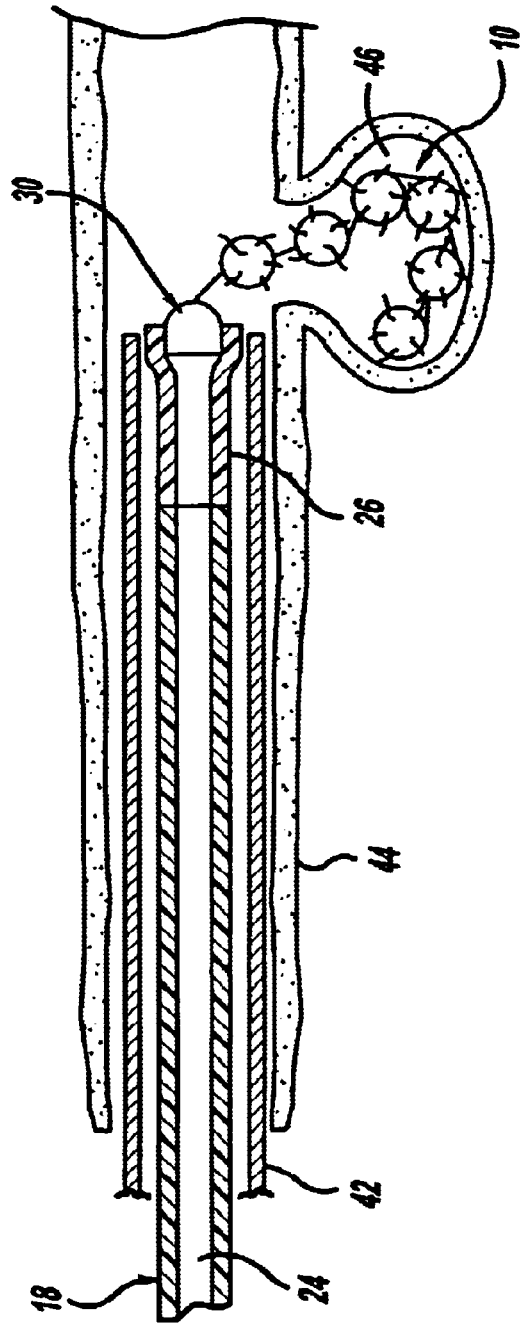
FIG. 4 is an enlarged, partially sectioned view showing the aneurysm embolization device being positioned within a high volume aneurysm.
Figure 5:
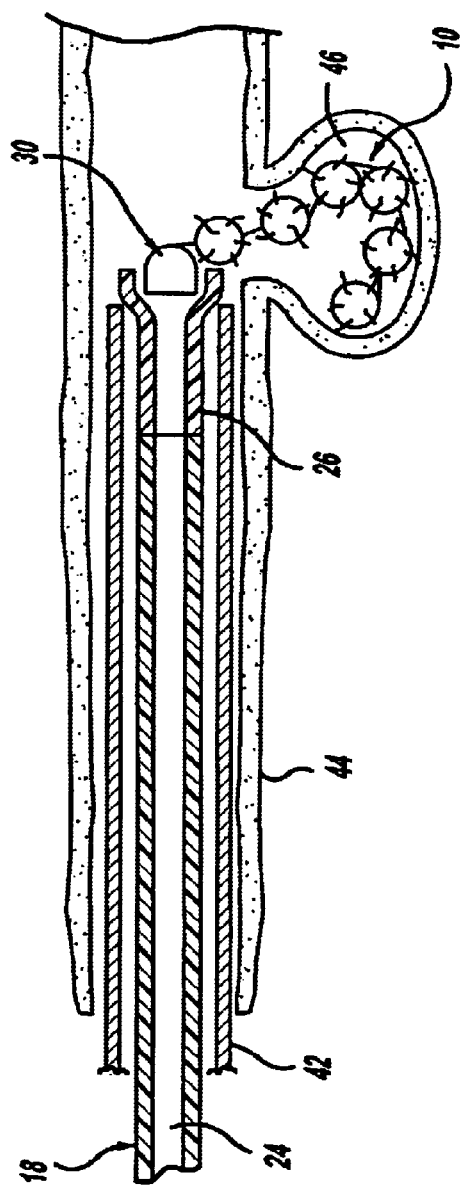
FIG. 5 is an enlarged, partially sectioned view showing radial expansion of the distal section of the deployment catheter thereby releasing the aneurysm embolization device; and, FIG. 6 is an enlarged, partially sectioned view of the aneurysm embolization device deployed within the high volume aneurysm causing the flow of blood within the aneurysm to occlude.

FIGS. 4 and 5 illustrate the deployment catheter 18 with the aneurysm embolization device 10 being positioned within an aneurysm 46. More particularly, as shown in FIG. 5, when fluid pressure is applied to the lumen 24 of the deployment catheter 18 the relatively low durometer distal section 26 of the deployment catheter 18 expands radially. As the distal section 26 of the deployment catheter 18 continues to expand radially there comes a point in which the headpiece 30 becomes disengaged from the lumen 24 of the deployment catheter 18 and the aneurysm embolization device 10 deploys within the aneurysm 46.

Figure 6:
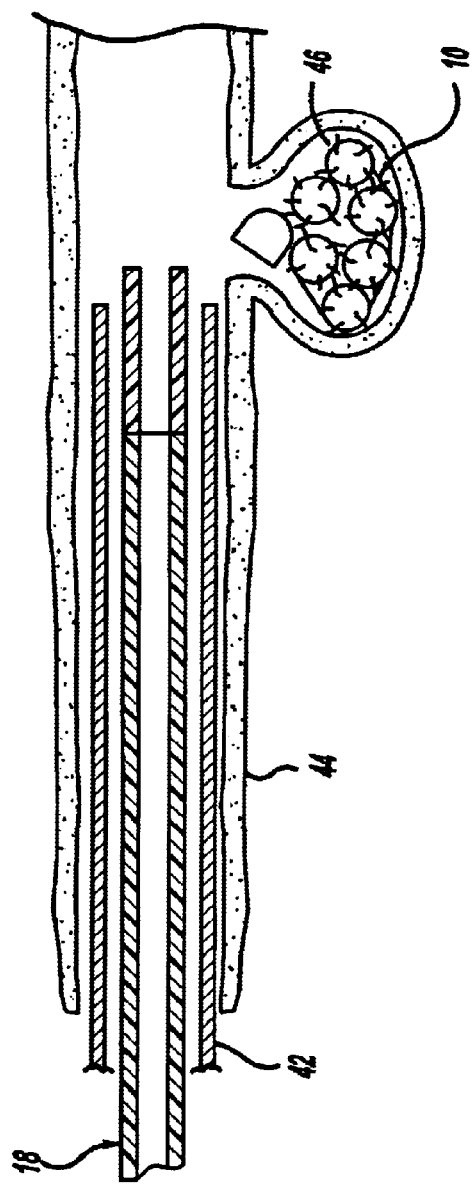

As illustrated in FIG. 6, when the aneurysm embolization device 10 has been released from the deployment catheter 18, the deployment catheter 18 may be withdrawn, leaving the aneurysm embolization device 10 positioned within the aneurysm 46 to occlude the flow of blood.

A novel system has been disclosed in which an aneurysm embolization device is delivered precisely to an aneurysm. Although a preferred embodiment of the invention has been described, it is to be understood that various modifications may be made by those skilled in the art without departing from the scope of the present invention. For example, there are many variations as to the number of spherical members and diameter of the spherical members. The number of spherical members and size of the spherical members would depend on what the physician requires for treating a particular aneurysm.

In an alternative construction, the aneurysm embolization device could include pockets on the spherical members. The pockets may take the form of concave indentations positioned on the spherical member where the central connecting member attaches to the spherical member. During deployment of the aneurysm embolization device, the central connecting member can coil up into the pockets on the spherical member.

Furthermore, the aneurysm embolization device could include perpendicular wire branches between the spherical members with their own set of spherical members. These perpendicular branches and additional spherical members could further enhance the occluding effect of the aneurysm embolization device.

In another alternative construction, the aneurysm embolization device could include spherical members which are free floating along the central connecting member between the headpiece and most distal spherical member. These free floating spherical members could have channels through their centers which would allow the spherical members to slide along the central connecting member thereby allowing the aneurysm embolization device to assume complex configurations to fill an aneurysm.

These and other modifications would be apparent to those having ordinary skill in the art to which this invention relates and are intended to be within the scope of the claims which follow.

That which is claimed is:

1. An aneurysm embolization device and deployment system for use in placing said embolization device at a preselected position within a vessel of a human body, said embolization device and deployment system comprising:

a deployment catheter having a small diameter lumen extending therethrough and having a proximal section and a distal section, said catheter being formed of a material which is sufficiently flexible to pass through the vessel of the body, the proximal section of said catheter exhibiting the characteristic of having substantially no radial expansion when fluid pressure is applied to the lumen of said catheter, and the distal section of said catheter exhibiting the characteristic that, when fluid pressure is applied to the lumen of said catheter the distal section of said catheter expands radially;

a headpiece having a proximal section and a distal section, the distal section of said headpiece takes the form of a hemisphere and the proximal section of said headpiece takes the form of a cylinder;

a central connecting member which takes the form of a flexible fiber, said connecting member having a proximal end and a distal end, the proximal end of said connecting member being attached to the distal section of said headpiece;

a spherical member which takes the form of a small diameter ball, said spherical member being disposed about the distal end of said central connecting member;

a connector coupled to the proximal section of said deployment catheter and adapted for a fluid pressure generating device; and, said proximal section of said headpiece being disposed within the distal section of said deployment catheter so that when a fluid pressure is applied to the lumen of said catheter the distal section of said catheter expands radially thereby releasing said headpiece.

2. An aneurysm embolization device and deployment system as defined in claim 1, wherein said headpiece and said spherical member are made of a polymer material.

3. An aneurysm embolization device and deployment system as defined in claim 1, wherein said headpiece and said spherical member are made of a metallic material.

4. An aneurysm embolization device and deployment system as defined in claim 1, wherein said central connecting member takes the form of a shape memory wire such that, after said wire is deployed at the preselected position within the vessel said wire tends to assume a predetermined configuration.

5. An aneurysm embolization device and deployment system as defined in claim 1, wherein said central connecting member takes the form of a stretchable fiber.

6. An aneurysm embolization device and deployment system as defined in claim 1, wherein said headpiece includes a pocket which takes the form of a concave indentation on said headpiece at a position where said central connecting member attaches to said headpiece, so that said central connecting member can coil up into said pocket during deployment.

7. An aneurysm embolization device and deployment system as defined in claim 1, wherein said spherical member includes a plurality of flexible filaments being attached generally radial to said spherical member, so that the occlusive effect of said spherical member is enhanced.

8. An aneurysm embolization device and deployment system as defined in claim 1, wherein said spherical member includes a time-released adhesive on the periphery of said spherical member, so that the occlusive effect of said spherical member is enhanced.

9. An aneurysm embolization device and deployment system as defined in claim 1, wherein said aneurysm embolization device includes six spherical members.

10. An aneurysm embolization device for use in occluding the flow of blood at a preselected position within a vessel, said embolization device comprising:
    a headpiece having a proximal section and a distal section, the distal section of said headpiece takes the form of a hemisphere and the proximal section of said headpiece takes the form of a cylinder;
    a central connecting member which takes the form of a flexible fiber, said connecting member having a proximal end and a distal end, the proximal end of said connecting member being attached to the distal section of said headpiece; and,
    a spherical member which takes the form of a small diameter ball, said spherical member being disposed about the distal end of said central connecting member.

11. An aneurysm embolization device as defined in claim 10, wherein said headpiece and spherical member are made of a polymer material.

12. An aneurysm embolization device as defined in claim 10, wherein said headpiece and said spherical member are made of a metallic material.

13. An aneurysm embolization device as defined in claim 10, wherein said central connecting member takes the form of a shape memory wire such that, after said wire is deployed at the preselected position within the vessel said wire tends to assume a predetermined configuration.

14. An aneurysm embolization device as defined in claim 10, wherein said central connecting member takes the form of a stretchable fiber.

15. An aneurysm embolization device as defined in claim 10, wherein said spherical member includes a plurality of flexible filaments being attached generally radial to said spherical member, so that the occlusive effect of said spherical member is enhanced.

16. An aneurysm embolization device as defined in claim 10, wherein said spherical member includes a time-released adhesive on the periphery of said spherical member, so that the occlusive effect of said spherical member is enhanced.

17. An aneurysm embolization device as defined in claim 9, wherein said aneurysm embolization device has six spherical members.

18. A method for placing an aneurysm embolization device at a pre-selected position within a vessel, the method comprising the steps of:
    providing a delivery catheter comprising an elongated flexible tube with a lumen extending therethrough;
    introducing said deliver catheter into the vasculature of the human body;
    providing a deployment catheter having a small diameter lumen extending therethrough and having a proximal section and a distal section, said catheter being formed of a material which is sufficiently flexible to pass through the vessel of the body, the proximal section of said catheter exhibiting the characteristic of having substantially no radial expansion when fluid pressure is applied to the lumen of said catheter, and the distal section of said catheter exhibiting the characteristic that, when fluid pressure is applied to the lumen of said catheter the distal section of said catheter expands radially;
    providing an aneurysm embolization device comprising a headpiece having a proximal section and a distal section, the distal section of said headpiece takes the form of a hemisphere, the proximal section of said headpiece takes the form of a cylinder and is disposed within said deployment catheter; said embolization device also comprising a central connecting member which takes the form of a flexible fiber, said connecting member having a proximal end and a distal end, the proximal end of said connecting member being attached to the distal section of said headpiece; said embolization device also comprising a spherical member which takes the form of a small diameter ball, said spherical member being disposed about the distal end of said central connecting member;
    introducing said deployment catheter and said aneurysm embolization device into said delivery catheter and aligning said aneurysm embolization device with said pre-selected position within said vessel; and,
    applying fluid pressure to said deployment catheter causing the distal section of the said deployment catheter to expand radially and thereby cause the aneurysm embolization device to release from said deployment catheter.

* * * * *